(12) United States Patent
Sun et al.

(10) Patent No.: US 9,093,412 B2
(45) Date of Patent: Jul. 28, 2015

(54) APPARATUS AND METHOD FOR TESTING PAD CAPACITANCE

(75) Inventors: Linda K. Sun, Fremont, CA (US); Harry Muljono, San Ramon, CA (US)

(73) Assignee: Intel Corporation, Santa Clara, CA (US)

( * ) Notice: Subject to any disclaimer, the term of this patent is extended or adjusted under 35 U.S.C. 154(b) by 675 days.

(21) Appl. No.: 13/332,285

(22) Filed: Dec. 20, 2011

(65) Prior Publication Data

US 2013/0154677 A1    Jun. 20, 2013

(51) Int. Cl.
    *G01R 31/3187*  (2006.01)
    *H01L 21/66*    (2006.01)
    *G01R 31/28*    (2006.01)

(52) U.S. Cl.
    CPC ............ *H01L 22/34* (2013.01); *G01R 31/2884* (2013.01)

(58) Field of Classification Search
    None
    See application file for complete search history.

(56) References Cited

U.S. PATENT DOCUMENTS

| | | | | |
|---|---|---|---|---|
| 5,179,345 A | * | 1/1993 | Jenkins et al. | 324/678 |
| 5,561,381 A | * | 10/1996 | Jenkins et al. | 324/678 |
| 7,638,749 B2 | * | 12/2009 | Fowler | 250/214 R |

* cited by examiner

*Primary Examiner* — Paresh Patel
(74) *Attorney, Agent, or Firm* — Schwabe, Williamson & Wyatt, P.C.

(57) ABSTRACT

A pad capacitance test circuit may be coupled to one or more pads of an electronic circuit, such as a processor. The pad capacitance test circuit may be located on a die including the electronic circuit. The pad capacitance test circuit may reset a pad voltage of one or more of the pads to zero, and then couple the pad to a supply voltage through a pullup resistor for a time period. The final pad voltage at or near the end of the period of time may be measured. The pad capacitance may be determined from the measured value of the final pad voltage and known values of the supply voltage, the time period, and resistance of the pullup resistor.

13 Claims, 4 Drawing Sheets

APPARATUS AND METHOD FOR TESTING PAD CAPACITANCE

TECHNICAL FIELD

This disclosure relates generally to electronic circuits. More particularly but not exclusively, the present disclosure relates to apparatuses and methods for testing pad capacitance of electronic circuits.

BACKGROUND INFORMATION

Many electronic circuits, such as processor chips, have one or more pads for input and/or output (I/O) of data and/or other signals between the circuit and other devices. In the case of a processor, the processor is often printed on a silicon die, and the die is placed in a package. The pads of the processor are coupled to corresponding pins on the package. The pad capacitance is a parameter usable for evaluating I/O performance. Currently, pad capacitance is measured using a time-domain reflectometry (TDR) method after the circuit is printed on silicon. In the TDR method, a signal is sent through a pin and the reflected signal is evaluated. However, the TDR method requires the circuit to be turned off and is limited to measuring the pad capacitance under one set of process, voltage and temperature (PVT) conditions (e.g., in one PVT corner). Furthermore, the test process is time consuming, and is therefore only performed on a few units of a batch of circuits. Accordingly, the pad capacitance data that is collected is limited and contains substantial margin for error. Additionally, the data is measured at the pin, and package traces can introduce additional error.

BRIEF DESCRIPTION OF THE DRAWINGS

Non-limiting and non-exhaustive embodiments are described with reference to the following figures, wherein like reference numerals refer to like parts throughout the various views unless otherwise specified.

DETAILED DESCRIPTION

Embodiments of a method and apparatus for testing pad capacitance are described herein. In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Various embodiments provide a pad capacitance test circuit and a method of testing pad capacitance. The test circuit may be coupled to one or more pads of an electronic circuit (e.g., a processor), to test the capacitance of the one or more pads. In one embodiment, the test circuit may be located on a die (e.g., a silicon die) that includes the electronic circuit to be tested. The pad capacitance test circuit may allow the pad capacitance to be tested on die without error from package traces. Additionally, the pad capacitance may be tested across process, voltage, and temperature (PVT) corners. Furthermore, the pad capacitance test circuit may allow large volume testing of electronic circuits, thereby allowing the electronic circuits to be screened for pad capacitance prior to shipment and/or allowing collection of variation data across units of the electronic circuit.

In one embodiment, a testing apparatus may include an electronic circuit disposed on a die, the electronic circuit including one or more pads. The testing apparatus may further include a test circuit disposed on the die and configured to couple a first pad of the one or more pads to a supply voltage for a time period, the first pad being coupled to the supply voltage through a pullup resistor, and measure a first voltage of the first pad at a first time point at or near the end of the time period to enable a capacitance of the first pad to be determined.

In one embodiment, the test circuit may be further configured to reset a voltage level of the first pad to approximately zero voltage prior to the first pad being coupled to the supply voltage.

In one embodiment, a testing method may include resetting a voltage level at a pad, by a test circuit disposed on a die that includes the pad; coupling the pad to a supply voltage through a pullup resistor for a time period; and determining the voltage level of the pad at or near the end of the time period.

In one embodiment, a computing apparatus may include a processor disposed on a die and having one or more pads, and a test circuit disposed on the die. The test circuit may include a pulldown device coupled to a first pad of the one or more pads, the pulldown device being configured to receive a reset signal and to turn on a conductive path between the first pad and a ground terminal in response to the reset signal; a pullup resistor having a first terminal and a second terminal, the first terminal being coupled to the first pad and the second terminal being coupled to a pullup node; and a pullup device coupled between the pullup node and a supply node, the supply node being configured to receive a supply voltage, and the pullup device being configured to receive a pullup signal and to turn on a conductive path between the supply node and the pullup node for a time period in response to the pullup signal.

Figure 1:
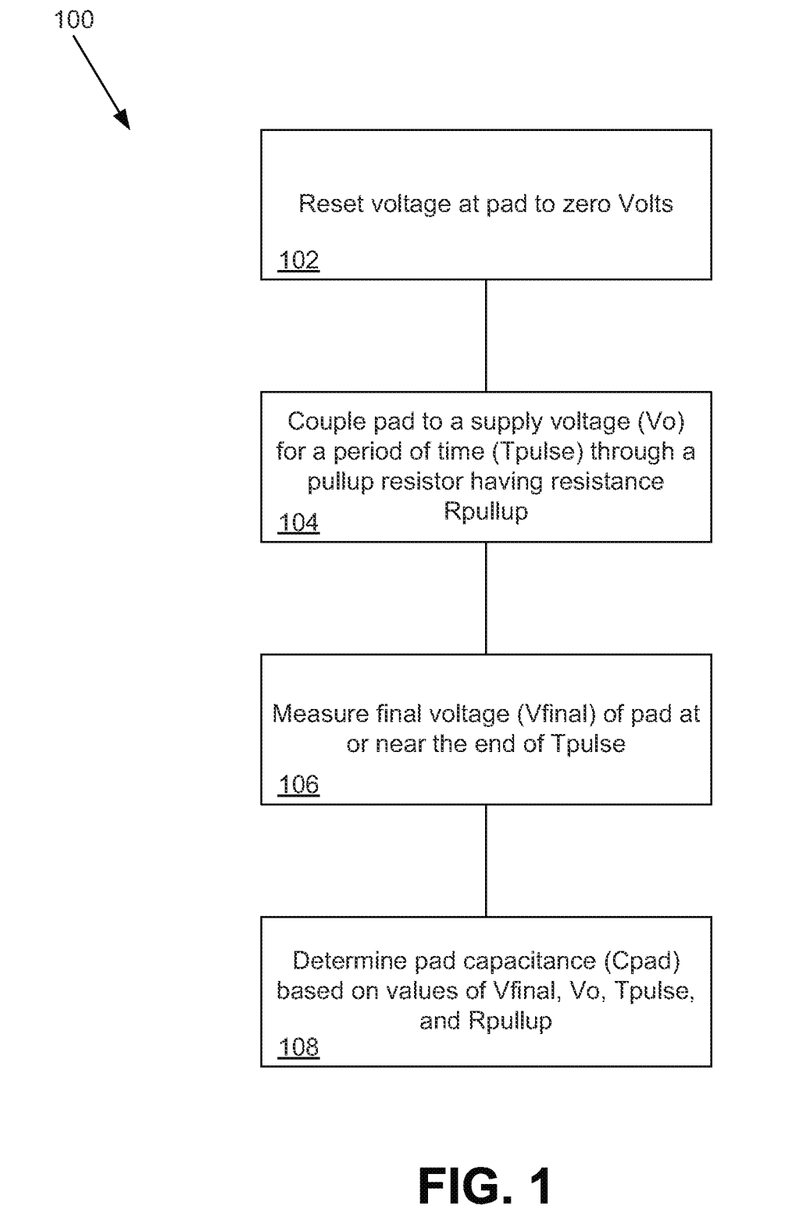
FIG. 1 is a block diagram of a method for testing pad capacitance in accordance with various embodiments.

FIG. 1 illustrates a method 100 of testing the pad capacitance, Cpad, of one or more pads of an electronic circuit, in accordance with various embodiments. At 102, the voltage of the pad may be brought to a pad voltage of zero Volts (also referred to as a "reset" of the pad voltage). For example, the pad may be coupled to a ground terminal. At 104, the pad may be coupled to a supply voltage, Vo, for a period of time, Tpulse, through a pullup resistor, Rpullup, coupled to the pad. The values of Vo, Tpulse, and Rpullup may all be known values. At 106, a final voltage (also referred to as a first voltage), Vfinal, which is the pad voltage at or near the end of Tpulse, may be measured. The value of Vfinal at the end of Tpulse may be given by the following Equation (1) in one embodiment:

$$V\text{final} = V_0 * (1 - e^{-Tpulse/(Rpullup*Cpad)})$$

Since the values of Vo, Tpulse, and Rpullup are known, the pad capacitance (Cpad) may be determined, at 108, based on Equation (1) and the measured value of Vfinal.

In some embodiments, the value of Rpullup may be determined by measuring the resistance of a calibration resistor having the same nominal resistance value as the pullup resistor. For example, the resistance of the calibration resistor may be determined by placing a known voltage across the calibration resistor and measuring the resulting current and/or placing a known current through the calibration resistor and measuring the resulting voltage drop across the calibration resistor. The calibration of the resistance value of Rpullup may allow the Rpullup value to be adjusted for natural variation in resistance of Rpullup (e.g., from different PVT conditions).

In some embodiments, the value of Vfinal may be measured at 106 by repeating the resetting at 102 and coupling to the supply voltage at 104 (collectively referred to as the pullup procedure) in a plurality of iterations. In each iteration, the pad voltage at or near the end of Tpulse may be compared to a reference voltage produced by a voltage reference generator located on the die. The reference voltage may be adjusted (e.g., increased and/or decreased) with each successive iteration of the pullup procedure. The value of Vfinal may be determined based on the value of the reference voltage if the result of the comparison changes from a first logical state to a second logical state (e.g., from a logic 0 to a logic 1). Determining the value of Vfinal by comparing the pad voltage to a reference voltage produced on-die may provide an accurate measurement and prevent/reduce error from package traces.

In some embodiments, the value of the pad capacitance determined by method 100 may be used to sort the electronic circuits (e.g., allow only electronic circuits having a pad capacitance within a specified range to be sent to customers). In some embodiments, method 100 may be repeated under various PVT conditions to gather pad capacitance data for different PVT conditions. Method 100 may be performed while the electronic circuit being tested is powered on, thereby allowing pad capacitance data to be gathered across PVT corners.

Figure 2:
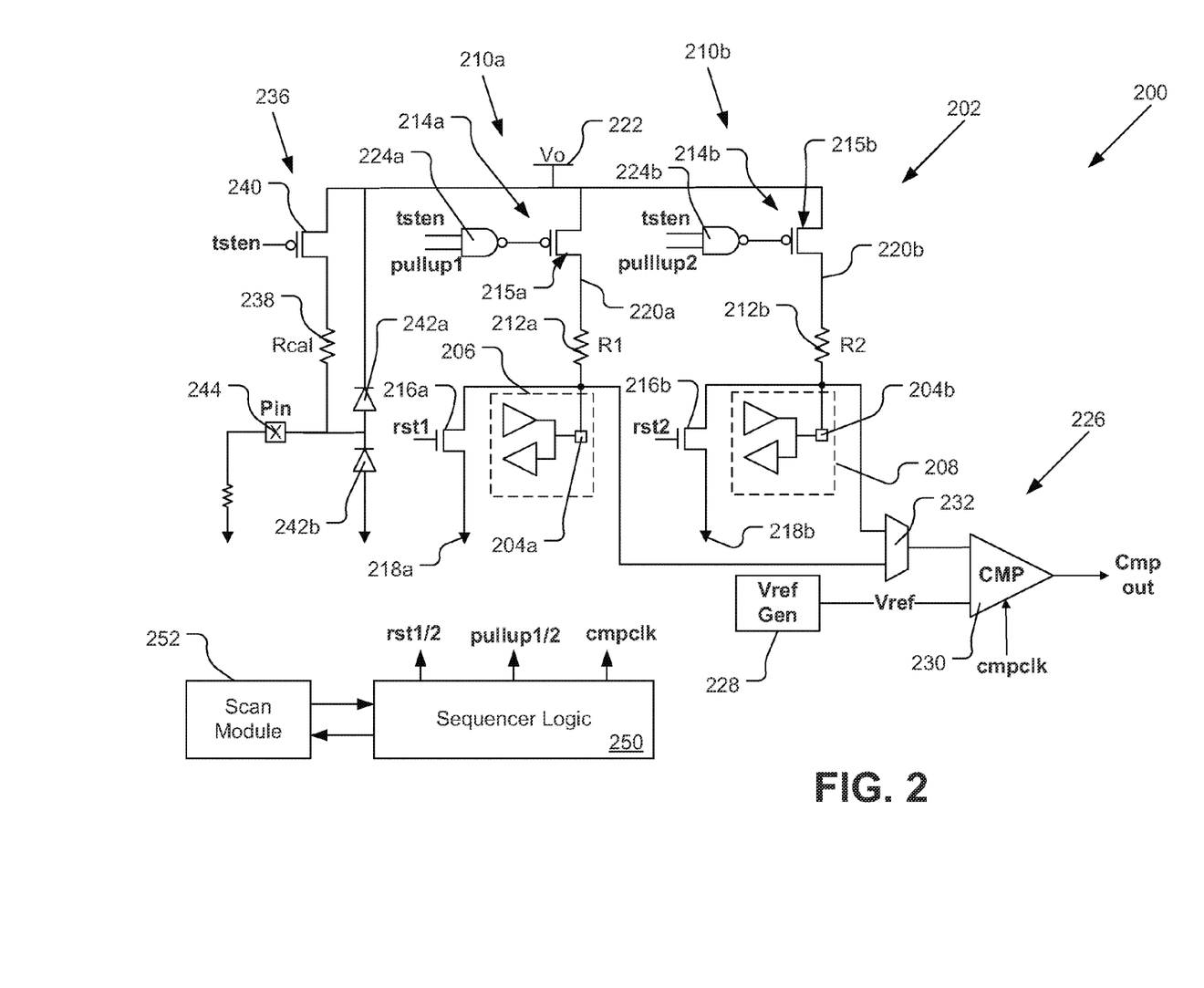
FIG. 2 is a circuit diagram that illustrates a pad capacitance test circuit, scan module, and sequencer logic module in accordance with various embodiments.

FIG. 2 illustrates a circuit 200 in accordance with various embodiments. In some embodiments, circuit 200 may be configured to carry out method 100.

Circuit 200 may include a test circuit 202 coupled to one or more pads 204a-b of an electronic circuit, such as a processor. The pads 204a-b may be coupled to one or more I/O circuits of the electronic circuit, such as a first I/O circuit 206 and a second I/O circuit 208, respectively. In one embodiment, the first I/O circuit 206 may be a double data rate (DDR) I/O circuit, and/or the second I/O circuit 208 may be a combination QuickPath Interconnect/Peripheral Component Interconnect Express (QPI/PCIe) circuit. The pad capacitance of these I/O circuits 206 and 208 may be usable to evaluate I/O performance of the processor. In other embodiments, the test circuit 202 may be coupled to any combination of one or more pads of the electronic circuit to test the capacitance of the pads.

Test circuit 202 may include one or more test modules 210a-b coupled to respective pads 204a-b. Test modules 210a-b may include a pullup resistor 212a-b, a pullup device 214a-b, and a pulldown device 216a-b. In other embodiments, one or more components of test modules 210a and/or 210b may be shared by a plurality of test modules 210a-b. Pullup resistors 212a-b may have a resistance, Rpullup. The value of Rpullup may be known or may be determined from a calibration module as described below.

Pulldown device 216a-b may be coupled to pad 204a-b and may receive a reset signal (e.g., rst1, rst2). The reset signal may selectively control the pulldown device 216a-b to bring the voltage at the pad 204a-b to a zero voltage (e.g., ground). For example, the pulldown device 216a-b may be embodied as a transistor (e.g., an n-type transistor) with the drain coupled to the pad 204a-b, the source coupled to a ground terminal 218a-b, and the gate configured to receive the reset signal. During a reset operation, the reset signal may transition from a first logic state to a second logic state (e.g., a logic 0 to a logic 1), thereby turning on the pulldown device 216a-b to operatively couple the pad 204a-b to the ground terminal 218a-b and bring the voltage at the pad 204a-b to zero Volts.

Each pullup resistor 212a-b may be coupled between the pad 204a-b and a pullup node 220a-b. The pullup device 214a-b may be coupled between the pullup node 220a-b and a supply node 222. A supply voltage, Vo, may be present at the supply node 222. The pullup device 214a-b may receive a pullup signal (e.g., a pulse signal) that switches from a first logic state to a second logic state (e.g., from a logic 0 to a logic 1) for a time period, Tpulse. The pullup device 214a-b may be turned on if the pullup signal received by the pullup device 214a-b has the second logic state (e.g., logic 1), thereby allowing current to flow from the supply node 222 to the pullup node 220a-b and raising (e.g., "pulling up") the voltage at the pullup node 220a-b to at or near the supply voltage Vo for the time period Tpulse.

For example, as shown in FIG. 2, the pullup device 214a-b may include a transistor 215a-b (e.g., a p-type transistor), with the source coupled to the supply node 222, the drain coupled to the pullup node 220a-b, and the gate configured to receive the pullup signal. In some embodiments, the pullup device 214a-b may further include activation logic 224a-b. The activation logic 224a-b may receive the pullup signal (e.g., pullup1, pullup2) and an enable signal (tsten), and may allow the pullup signal to turn on the transistor 215a-b if the enable signal is turned on (e.g., at a logic 1). For example, the NAND gate may pass a logic 0 to the p-type transistor 215a-b (thereby turning on the p-type transistor) if the pullup signal is a logic 1 and the enable signal is a logic 1. If the pullup signal switches from the first logic state to the second logic state such that a logic 0 is received at the gate, the p-type transistor 215a-b may turn on, thereby allowing current to flow from the supply node 222 to the pullup node 220a-b and raising the voltage at the pullup node 220a-b to at or near the supply voltage, Vo.

The configuration of pullup devices 214a-b (e.g., transistors 215a-b and activation logic 224a-b) shown in FIG. 2 is merely an example, and many other configurations of devices (e.g., p-type and/or n-type, NAND gate and/or AND gate) may be used. In various embodiments, the transistor 215a-b may receive the pullup signal directly and/or through other devices.

In various embodiments, the test circuit 202 may further include a measurement module 226 to measure the voltage at the pad 204a-b. The measurement module 226 may measure the voltage, Vfinal, of the pad 204a-b at or near the end of the pulse in the pullup signal (e.g., when the pullup signal switches back from the second logic state to the first logic state, or otherwise switches state). The capacitance of the pad, Cpad, may then be calculated by Equation (1) using known values for Vfinal, Vo, Tpulse, and Rpullup.

In some embodiments, the measurement module 226 may include a voltage reference generator 228 and a comparator 230. The comparator 230 may receive the pad voltage and compare the pad voltage to a reference voltage, Vref, produced by the voltage reference generator 228. The comparator 230 may receive a comparator clock signal Cmpclk to control the timing of the comparison to be at or near the end of the time period Tpulse. A result of the comparator 230 at the time of receiving the comparator clock signal Cmpclk may be output as a comparator output signal Cmpout. In embodiments in which the test circuit 202 is coupled to more than one pad 204a-b, the pads 204a-b may be coupled to a multiplexer 232 which may be used to select the current pad under test and to pass the corresponding pad voltage to the comparator 230.

In some embodiments, the comparator 230 may determine Vfinal using an iterative method. Multiple iterations of the pullup procedure described above may be performed (e.g., resetting the pad voltage to zero and then pulling up the pullup node for Tpulse and passing the pad voltage to the comparator 230). With each successive iteration of the pullup procedure, the voltage reference generator may increase the voltage level of Vref. If Vfinal is equal to or greater than Vref, the output signal of the comparator 230 switches from the output signal of the prior iteration (e.g., from a logic 0 to a logic 1). Accordingly, the value of Vfinal may be determined based on the voltage level of Vref for the iteration in which the output signal of the comparator 230 switches. For example, Vfinal may be assigned a value equal to the voltage level of Vref during the iteration in which the comparator 230 output switches, and/or may be assigned a value between that iteration and the prior iteration (e.g., the midpoint). In some embodiments, further iterations may not be performed after the output signal of the comparator 230 switches. In other embodiments, further iterations may be performed, e.g., to validate the result.

In one embodiment, Vref may be increased from about 200 millivolts (mV) to about 800 mV, rising in increments of about 5 to 10 mV with each successive iteration of the pullup procedure. In other embodiments, any suitable voltage range and/or voltage increment may be used. For example, the voltage range and/or voltage increment used may be selected based on expected value of Vfinal, desired accuracy of the measurement, and/or time requirements.

In some embodiments, the test circuit 202 may further include a calibration module 236 to calibrate the value of Rpullup. The calibration module 236 may include a calibration resistor 238 having a nominal resistance value that is substantially similar to a nominal resistance value of the pullup resistors 212a-b (e.g., substantially equal to Rpullup). The calibration module 236 may measure the resistance of the calibration resistor 238 to determine Rpullup. The calibration may facilitate accurate measurements and/or may account for variance in the resistance of Rpullup depending on various conditions, such as process, voltage, and/or temperature. However, in other embodiments, a known nominal value of Rpullup may be used in the calculations.

The value of Rpullup may be determined by any suitable method. For example, as shown in FIG. 2, the calibration module 236 may include a switch 240 (e.g., a transistor 240), diodes 242a-b, and an external pin 244. The transistor 240 receives the enable signal, tsten, which selectively turns on the transistor 240.

If the transistor 240 is on, a known voltage is dropped across the calibration resistor 238. The current may be measured at the external pin 244, and the value of Rpullup may be determined accordingly.

In various embodiments, the test circuit 200 may further include a sequencer logic module 250 to provide the enable signal, pullup signals (e.g., pullup1 and pulllup2), reset signals (e.g., rst1 and rst2), and/or comparator clock (e.g., Cmpclk) to control the test circuit 202 with suitable timing. The sequencer logic module 250 may be configured to produce the reset signal, then produce the pullup signal soon after the reset signal, and then produce the comparator clock signal soon after the pullup signal. This may facilitate accurate measurement of Vfinal (e.g., by preventing/reducing leakage between operations). The operation of sequencer logic module 250 is discussed in more detail below with respect to FIG. 3.

The test circuit 200 may further include a scan module 252. Scan module 252 may be coupled to a control pin (not shown) of the die. The scan module 252 may facilitate input and/or output of controls and/or data between circuit 200 and an external control device. The scan module 252 may allow the input and/or output to be performed using a single control pin, thereby keeping the pin requirements to a minimum. In other embodiments, a plurality of pins may be used for input and/or output of controls and/or data.

Figure 3:
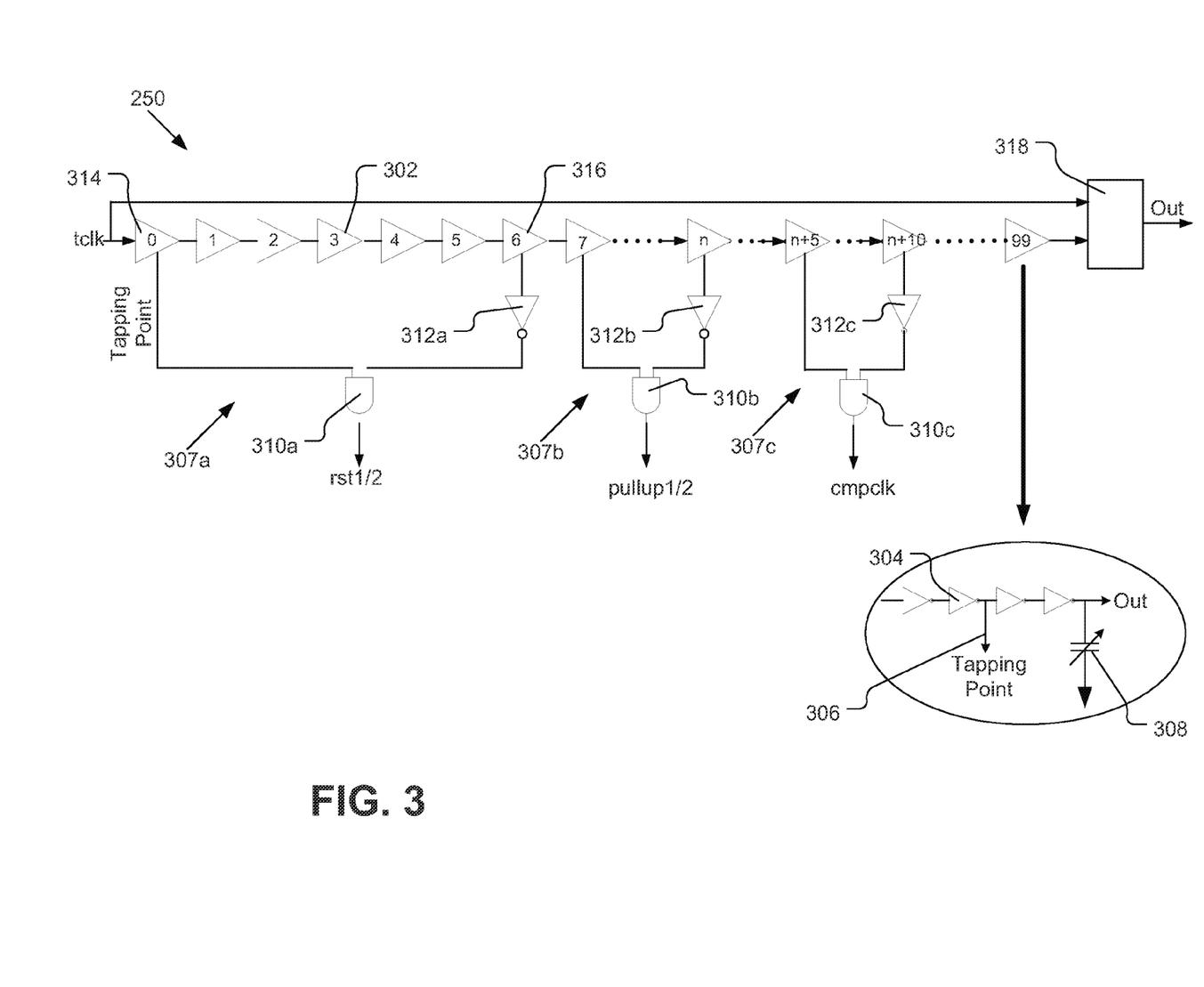
FIG. 3 is a block diagram of an embodiment of the sequencer logic module shown in FIG. 2.

FIG. 3 illustrates an embodiment of the sequencer logic module 250 in more detail. Sequencer logic module 250 may include a plurality of delay-based buffers 302 coupled in series. For example, sequencer logic module 250 is shown in FIG. 3 with 100 buffers 302 (e.g., buffer0, buffer1, . . . , buffer99). Other embodiments may include any suitable number of buffers 302. The buffers 302 may include one or more inverters 304 coupled in series. For example, one or more of buffers 302 may include four inverters 304 coupled in series, as shown in the breakout window in FIG. 3. In other embodiments, buffers 302 may include any suitable number of inverters 304. In some embodiments, buffers 302 may include an even number of inverters 304 to facilitate extraction of a pulse signal, although an odd number 304 may also be used. Buffers 302 may further include a tapping point 306 to which extraction logic may be coupled to produce the control signals.

The series of buffers 302 may receive an input signal, tclk, which may be a square wave. Each buffer 302 may add a delay to the input signal tclk and pass the delayed signal the next buffer 302. One or more of the control signals, such as one or more reset signals, one or more pullup signals, and/or one or more comparator clock signals may be extracted from the sequencer logic 250. Any sequence of one or more buffers 302 may be used to produce the control signals. Extraction logic 307a-c may be coupled to a pair of buffers 302 (e.g., a start buffer and an end buffer) at their tapping points to extract a control signal that is a pulse signal having a pulse width approximately proportional to a total quantity of buffers 302 across which the extraction logic is coupled. Although the tapping points are shown in FIG. 3 to be between elements inside the buffer 302 (e.g., between the second and third inverters), in other embodiments the tapping point may be between adjacent buffers 302.

In some embodiments, each of the buffers 302 may include a tunable capacitor 308 to adjust the time delay provided by the buffers 302. In one embodiment, the tuning capacitor 308 may be 4-bits tunable. The sequencer logic module 250 may include a latch 318 for calibrating the delay provided by each buffer 302. The latch 318 may receive the output signal from the series of buffers 302 and compare the output signal to the input signal tclk. The output from latch 302 may be used to adjust the delay provided by buffers 302 (e.g., by adjusting tunable capacitors 308), until the total delay of the series of buffers 302 is substantially equal to a period of the input signal tclk. The capacitance of all of the tunable capacitors 308 may be adjusted together so that the delay provided by each buffer 302 is substantially the same. This calibration may facilitate the sequencer logic 250 producing the pullup signal with a known pulse width Tpulse. In one embodiment, the input signal tclk may be a square wave with a frequency of about 100 megahertz (MHz), and the series of buffers 302 may produce a total time delay of about 10 nanoseconds (ns).

In some embodiments, the extraction logic 307a-c may include an AND gate 310a-c and an inverter 312a-c to extract a control signal from a pair of buffers 302 (e.g., a start buffer and an end buffer), as shown in FIG. 3. Using extraction logic 307a as an example, a start buffer 314 may be coupled to a first input terminal of the AND gate 310a, and an end buffer 316 may be coupled to an input terminal of the inverter 312a-c. End buffer 316 may follow after start buffer 314 in the series of buffers 302. An output terminal of the inverter 312a-c may be coupled to a second input terminal of the AND gate 310a. This configuration may produce a pulse signal at an output terminal of the AND gate having a pulse width that is proportional to a total quantity of buffers 302 across which the AND gate 310a is coupled. The other extraction logic 307b-c may operate in a similar manner. In other embodiments, one or more of the extraction logic 307a-c may include any other suitable devices to extract a pulse signal from the buffers 302.

As shown in FIG. 3, extraction logic 307a may produce the reset signal, extraction logic 307b may produce the pullup signal, and extraction logic 307c may produce the comparator clock signal. The extraction logic 307a-c may be coupled to buffers 302 in a configuration that facilitates proper timing of the control signals. For example, the pullup signal may be transmitted to test circuit 202 soon after the reset signal is sent to test circuit 202. Accordingly, the start buffer (e.g., buffer7) used to produce the pullup signal may be immediately following and/or following soon after the end buffer (e.g., buffer6) used to produce the reset signal.

Similarly, the start buffer used to produce the comparator clock may be immediately following and/or following soon after the end buffer used to produce the pullup signal. For example, in FIG. 3, buffer(n) is the end buffer used to produce the pullup signal, and buffer(n+5) is the start buffer used to produce the comparator clock. In other embodiments, the start buffer used to produce the comparator clock may be in any suitable buffer following the end buffer used to produce the pullup signal, such as the immediately following buffer (e.g., buffer(n+1)).

It will be apparent that the configuration of extraction logic 307a-c shown in FIG. 3 is provided as an example, and other embodiments may include extraction logic 307a-c coupled to buffers 302 in any suitable configuration.

In some embodiments, the sequencer logic module 250 may be configured to selectively produce one or more of a plurality of pullup signals having different pulse widths. For example, in one embodiment, the sequencer logic module 250 may produce four pullup signals, with each pullup signal having a different pulse width (e.g., 0.5 ns, 1 ns, 1.5 ns, and 2 ns, respectively). In some embodiments, the extraction logic used to produce the plurality of pullup signals may overlap. That is, the pullup signals may use one or more of the same buffers 302 to produce the pullup signals. For example, the different extraction logic may be coupled to the same start buffer and to different end buffers. The sequencer logic module 250 may select one of the pullup signals to send to test circuit 202 to pull up the pad under test. In some embodiments, the pullup signals may be coupled to a multiplexer (not shown) to select the pullup signal to use for the current test. The pullup signal may be selected based on any suitable factors, such as an expected capacitance of the pad under test, and/or results of previous iterations of the test procedure.

In some embodiments with multiple pullup signals, the sequencer logic module 250 may also be configured to selectively produce the comparator clock at a different set of buffers 203 depending on which pullup signal is used. This may facilitate having the comparator clock follow soon after the pullup signal to measure Vfinal at or near the end of the time period of the pullup signal, thereby preventing/reducing error from leakage.

In some embodiments, the comparator clock may be a first comparator clock, and the sequencer logic module 250 may produce a second comparator clock from a sequence of buffers 203 at or near the end of the series of buffers 203. The second comparator clock may be used to determine a leakage current of the pad under test. As discussed above, the first comparator clock may trigger the comparator to measure the voltage of the pad at a first time point at or near the end of the pulse of the pullup signal. The second comparator clock may trigger the comparator to measure the pad voltage at a second time point that is later in time than the first comparator clock. The pad voltage at the second time point may be measured by a similar iterative method as described above, using the second comparator clock to trigger the comparison of the pad voltage with the reference voltage. The pad voltage at the second time point may then be compared with the voltage level of the pad at the first time point to determine the leakage current of the pad. In some embodiments, the value of the leakage current may be used to sort and/or characterize the electronic circuits.

Figure 4:
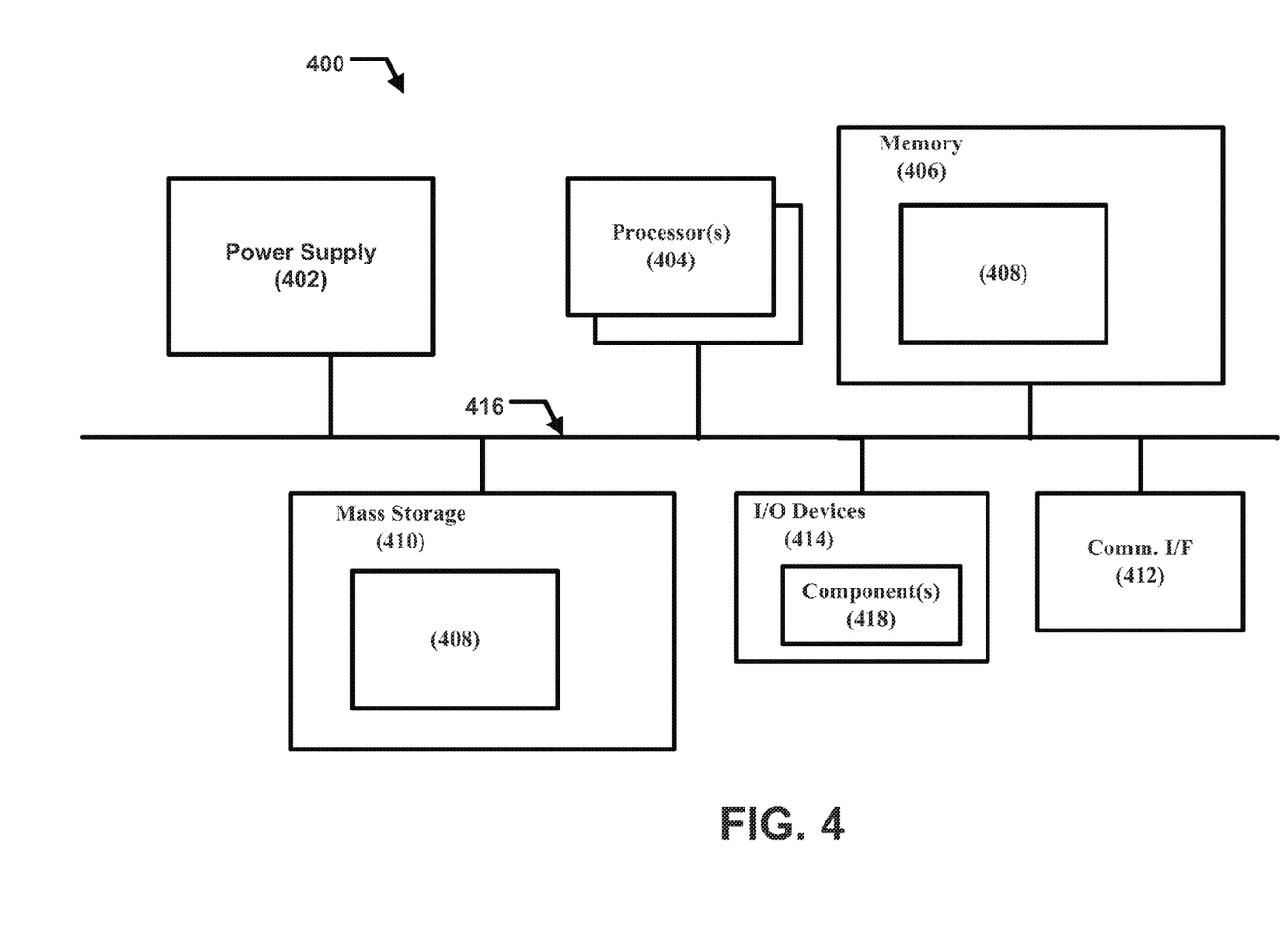
FIG. 4 is a block diagram that illustrates an example computer system suitable to practice the disclosed embodiments.

Embodiments of the method 100 and/or circuit 200 described herein may be used in a number of implementations and applications. For example, processor chips may include a circuit 200 disposed on the same die as the processor to measure the pad capacitance of one or more pads of the processor. The pad capacitance data may be used to sort processors (e.g., to prevent processors with a pad capacitance outside a suitable range from being shipped to a customer). For example, mobile devices, including but not limited to smart phones, nettops, tablets and other Mobile Internet Devices (MIDs) may have one or more processors having a pad capacitance test circuit. FIG. 4 is a block diagram that illustrates an example computer system 400 suitable to practice the disclosed disable circuit/method of various embodiments.

As shown, the computer system 400 may include a power supply unit 402, a number of processors or processor cores 404, a system memory 406 having processor-readable and processor-executable instructions 408 stored therein, a mass storage device 410 that may also store the instructions 408, and a communication interface 412. For the purpose of this application, including the claims, the terms "processor" and "processor cores" may be considered synonymous, unless the context clearly requires otherwise.

The one or more mass storage devices 410 and/or the memory 406 may comprise a tangible, non-transitory computer-readable storage device (such as a diskette, hard drive, compact disc read only memory (CDROM), hardware storage unit, and so forth). The computer system 400 may also comprise input/output devices 414 (such as a keyboard, display screen, cursor control, and so forth). According to various embodiments, one or more of the depicted components of the system 400 and/or other element(s) may include a keyboard, LCD screen, non-volatile memory port, multiple antennas, graphics processor, application processor, speakers, or other associated mobile device elements, including a camera.

In various embodiments, at least one processor 404 and/or other component(s) 418 may include a pad capacitance test circuit (such as the circuit 200 of FIG. 2).

The various elements of FIG. 4 may be coupled to each other via a system bus 416, which represents one or more buses. In the case of multiple buses, they may be bridged by one or more bus bridges (not shown). Data may pass through the system bus 416 through the I/O devices 414, for example, between the component(s) 418 and the processors 404.

The system memory 406 and the mass storage device 410 may be employed to store a working copy and a permanent copy of the programming instructions implementing one or more operating systems, firmware modules or drivers, applications, and so forth, herein collectively denoted as 408. The permanent copy of the programming instructions may be placed into permanent storage in the factory, or in the field, through, for example, a distribution medium (not shown), such as a compact disc (CD), or through the communication interface 412 (from a distribution server (not shown)).

The remaining constitution of the various elements of the computer system 400 is known, and accordingly will not be further described in detail.

The above description of illustrated embodiments, including what is described in the Abstract, is not intended to be exhaustive or to be limited to the precise forms disclosed. While specific embodiments and examples are described herein for illustrative purposes, various modifications are possible. For example, the configuration and connection of certain elements in various embodiments have been described above in the context of high/low values of signals, responses to rising/falling edges of signals, inverters to invert signals, P-type and N-type transistors, and so forth. In other embodiments, different configurations can be provided in view of whether N-type transistors are used instead of P-type transistors, whether or not certain signals are inverted, whether certain changes in state are triggered in response to falling edges instead of rising edges or vice versa, and so forth.

These and other modifications can be made in light of the above detailed description. The terms used in the following claims should not be construed to be limited to the specific embodiments disclosed in the specification.

What is claimed is:

1. A testing apparatus, comprising:
an electronic circuit disposed on an integrated circuit (IC) die, the electronic circuit including one or more input/output (I/O) pads to communicate with one or more other devices external to the apparatus; and
a test circuit disposed on the IC die and configured to:
reset a voltage level of a first pad of the one or more I/O pads to approximately zero voltage;
couple, after the voltage level of the first pad is reset, the first pad to a supply voltage for a time period; and
measure a first voltage of the first pad at a first time point at or near the end of the time period to determine a capacitance of the first pad.

2. The apparatus of claim 1, wherein the test circuit is configured to couple the first pad to the supply voltage through a pullup resistor.

3. The apparatus of claim 2, wherein the test circuit includes a calibration resistor having a same nominal value as a nominal value of the pullup resistor, and wherein the test circuit is further configured to measure a resistance value of the calibration resistor.

4. The apparatus of claim 1, wherein the test circuit includes a comparator and a voltage reference generator, and the test circuit is further configured to repeat the resetting and the coupling in successive iterations, wherein the voltage reference generator is configured to adjust a reference voltage in the successive iterations, and wherein the comparator is configured to compare the reference voltage to the first voltage to determine a value of the first voltage.

5. The apparatus of claim 1, further comprising a sequencer logic module disposed on the IC die and configured to:
produce a reset signal to trigger the test circuit to reset the voltage level of the first pad; and
produce a pullup signal to trigger the test circuit to couple the first pad to die supply voltage, the pullup signal being produced after an end of the reset signal.

6. The apparatus of claim 5, wherein the sequencer logic module is further configured to produce a comparator clock to trigger the test circuit to measure the first voltage, the comparator clock being produced after an end of the pullup signal.

7. The apparatus of claim 6, wherein the sequencer logic module includes:
a plurality of delay-based buffers coupled together in series and configured to receive an input clock signal;
a first extraction logic coupled to a first start buffer and a first end buffer of the plurality of buffers and configured to produce the reset signal, the reset signal having the first logic state for a first time period;
a second extraction logic coupled to a second start buffer and a second end buffer of the plurality of buffers and configured to produce the pullup signal, the pullup signal having the second logic state for a second time period; and
a third extraction logic coupled to a third start buffer and a third end buffer of the plurality of buffers and configured to produce the comparator clock signal, the comparator clock signal having the third logic state for a third time period;
wherein the second start buffer follows after the first end buffer and the third start buffer follows after the second end buffer in the series of buffers.

8. The apparatus of claim 1, wherein the test circuit is further configured to measure a voltage level of the first pad at a second time point after the first time point to determine a leakage current of the first pad.

9. A testing apparatus, comprising:
an electronic circuit disposed on a die, the electronic circuit including one or more pads;
a test circuit disposed on the die and configured to:
reset a voltage level of a first pad of the one or more pads to approximately zero voltage;
couple, after the voltage level of the first pad is reset, the first pad to a supply voltage for a time period; and
measure a first voltage of the first pad at a first time point at or near the end of the time period to enable a capacitance of the first pad to be determined; and a sequencer logic module disposed on the die, the sequencer logic module including:
a plurality of delay-based buffers coupled together in series and configured to receive an input clock signal;
a first extraction logic coupled to a first start buffer and a first end buffer of the plurality of buffers and configured to produce a reset signal to trigger the test circuit to reset the voltage level of the first pad, the reset signal having the first logic state for a first time period;
a second extraction logic coupled to a second start buffer and a second end buffer of the plurality of buffers and configured to produce a pullup signal to trigger the test circuit to couple the first pad to the supply voltage, the pullup signal being produced after an end of the reset signal, and the pullup signal having the second logic state for a second time period; and a third extraction logic coupled to a third start buffer and a third end buffer of the plurality of buffers and configured to produce a comparator clock signal to trigger the test circuit to measure the first voltage, the comparator clock being produced after an end of the pullup signal, the comparator clock signal having the third logic state for a third time period;

wherein the second start buffer follows after the first end buffer and the third start buffer follows after the second end buffer in the series of buffers.

10. The apparatus of claim 9, wherein the test circuit is configured to couple the first pad to the supply voltage through a pullup resistor.

11. The apparatus of claim 10, wherein the test circuit includes a calibration resistor having a same nominal value as a nominal value of the pullup resistor, and wherein the test circuit is further configured to measure a resistance value of the calibration resistor.

12. The apparatus of claim 9, wherein the test circuit includes a comparator and a voltage reference generator, and the test circuit is further configured to repeat the resetting and the coupling in successive iterations, wherein the voltage reference generator is configured to adjust a reference voltage in the successive iterations, and wherein the comparator is configured to compare the reference voltage to the first voltage to determine a value of the first voltage.

13. The apparatus of claim 9, wherein the test circuit is further configured to measure a voltage level of the first pad at a second time point after the first time point to determine a leakage current of the first pad.

* * * * *